(12) United States Patent
Franco et al.

(10) Patent No.: US 6,458,086 B1
(45) Date of Patent: Oct. 1, 2002

(54) IMPLANTABLE BLOOD FLOW MONITORING SYSTEM

(76) Inventors: Kenneth Lawrence Franco, 16603 Olde Country Rd., Apt. #3, Omaha, NE (US) 68118; Tofy Mussivand, 2616 Mer Bleue Road, Navan, Ontario (CA), K4B 1H9

( * ) Notice: Subject to any disclaimer, the term of this patent is extended or adjusted under 35 U.S.C. 154(b) by 0 days.

(21) Appl. No.: 09/543,618

(22) Filed: Apr. 5, 2000

(51) Int. Cl.[7] ................................................ A61B 5/02
(52) U.S. Cl. ........................ 600/526; 600/513; 600/454
(58) Field of Search .................................. 600/301, 407, 600/438, 454, 462, 468, 465, 504, 505, 509, 510, 513, 515, 519, 526, 527

(56) References Cited

U.S. PATENT DOCUMENTS

| | | | |
|---|---|---|---|
| 4,227,407 A | 10/1980 | Drost | |
| 4,414,980 A | 11/1983 | Mott | |
| 4,539,994 A | 9/1985 | Baumbach et al. | |
| 4,612,937 A | 9/1986 | Miller | |
| 5,058,592 A | 10/1991 | Whisler | |
| 5,220,924 A * | 6/1993 | Frazin | 128/662.06 |
| 5,267,569 A | 12/1993 | Lienhard | |
| 5,289,821 A | 3/1994 | Swartz | |
| 5,381,798 A | 1/1995 | Burrows | |
| 5,409,009 A | 4/1995 | Olson | |
| 5,423,323 A | 6/1995 | Orth | |
| 5,423,883 A * | 6/1995 | Helland | 607/127 |
| 5,458,122 A | 10/1995 | Hethuin | |
| 5,487,760 A * | 1/1996 | Villafana | 623/2 |
| 5,544,657 A | 8/1996 | Kurowski et al. | |
| 5,598,841 A | 2/1997 | Taniji et al. | |
| 5,598,847 A | 2/1997 | Renger | |
| 5,617,871 A | 4/1997 | Burrows | |
| 5,666,953 A * | 9/1997 | Wilk | 128/653.1 |
| 5,785,657 A | 7/1998 | Breyer et al. | |
| 5,785,660 A * | 7/1998 | van Lake et al. | 600/523 |
| 5,807,258 A | 9/1998 | Cimochowski et al. | |
| 5,853,368 A * | 12/1998 | Solomon et al. | 600/439 |
| 5,865,749 A | 2/1999 | Doten et al. | |
| 6,221,011 B1 * | 4/2001 | Bardy | 600/300 |
| 6,315,719 B1 * | 11/2001 | Rode et al. | 600/300 |
| 6,336,903 B1 * | 1/2002 | Bardy | 600/508 |

FOREIGN PATENT DOCUMENTS

| | | |
|---|---|---|
| GB | 2076963 A | 12/1981 |
| JP | 363275330 A | 11/1988 |
| JP | 401145046 A | 6/1989 |
| JP | 402121643 A | 5/1990 |
| JP | 403277351 A | 12/1991 |

* cited by examiner

*Primary Examiner*—Jeffrey R. Jastrzab
*Assistant Examiner*—Frances P. Oropeza
(74) *Attorney, Agent, or Firm*—Gifford, Krass, Groh, Sprinkle, Anderson & Citkowski, P.C.

(57) ABSTRACT

An implantable blood flow monitoring system for providing synchronized blood vessel flow and myocardial wall contractility data to an external monitor independent of transcutaneous leads. Synchronized electrocardiogram data allows and provides comprehensive monitoring. A means is provided for transmitting synchronized cardiac function data and blood flow data to a distant remote location to facilitate continual physician monitoring.

25 Claims, 2 Drawing Sheets

IMPLANTABLE BLOOD FLOW MONITORING SYSTEM

FIELD OF THE INVENTION

The present invention relates to medical diagnostic equipment and more particularly to an implantable monitoring device capable of displaying (a) blood flow and (b) heart wall motion information at a remote location or at a local location with no percutaneous holes or leads.

BACKGROUND OF THE INVENTION

Coronary artery disease (CAD) is a chronic condition requiring continuous management by a physician in order to prevent further cardiac damage and sudden death. Complications typical of coronary artery disease include angina, myocardial infarction, arrhythmia and heart failure due to loss of heart muscle. All of these complications diminish patient quality of life and without proper intervention can lead to death. Coronary artery disease is a major costly and devastating problem projected to be the preeminent health problem worldwide continuously going to year 2020 with in excess of 35 million sufferers. CAD patients that develop angina are initially treated medically with drugs and visit their physician on a regular basis provided the angina remains stable. For those individuals with resting angina, additional testing such as an angiogram and/or other tests are conducted with treatment involving either percutaneous transluminal coronary angioplasty (PTCA)/stent or coronary artery bypass grafting (CABG). Unfortunately, PTCA/stent patients often develop restenosis, requiring further testing and additional repeat procedures to correct recurrent angina. Alternatively, bypass grafts tend to occlude or otherwise develop stenoses over time resulting in recurrent angina, MI, arrhythmia, and heart failure which can lead to death. Myocardial infarctions associated with CAD afflict more than 1 million patients in the U.S. annually with many of which die suddenly therefrom worldwide with this estimate is over 3 million. As a result, CAD patients require regular physician maintenance visits to detect and possibly prevent complications and slow the debilitating effects thereof. Nonetheless, a risk of sudden and premature death from CAD remains as well as loss of heart function. Because very frequent follow up of each patient is impractical, expensive and can plague clinics and hospitals severely, there exists a need to prevent sudden death and the complications of CAD by monitoring of blood flow within coronary arteries.

Currently, the monitoring of blood flow within a native coronary artery or bypass graft requires the use of an angiogram. Intervention is dictated by a drop in blood flow which cause angina or by an MI as the native coronary artery or bypass graft occludes. An angiogram is an invasive test involving inherent risks associated with the imaging dye. Other angiogram associated risks include vascular complications such as stroke, emboli, ischemic leg, cardiac complications and renal damage. Without the ability to intervene early in the development of CAD, many unnecessary deaths result, as well as a diminished quality of life for patients owing to CAD complications resulting in huge economic losses and major expenses.

The dangers associated with an angiogram become more pressing with the increasing number of heart transplant operations performed especially if xenotransplantation is successful in the future. Approximately 50% of heart transplant recipients develop graft CAD within five years of the procedure. While heart transplant recipients do not develop angina owing to heart denervation during the transplant procedure, yearly or more frequent angiograms to diagnose the development of CAD are required with all the risks and expenses associated therewith. Further, heart transplant recipients bear an unacceptable risk of sudden death through myocardial infarction.

Periodic and/or continuous monitoring of coronary blood flow has been recognized as a means to allow early detection, management and intervention before CAD patients decompensate. Prior art attempts to continuously monitor blood flow have involved the implantation of a sensor with percutaneous leads exiting the patient to power and/or relay sensor data to an external monitor. Such prior devices have suffered from a variety of limitations that limit the usefulness thereof, these limitations having illustratively included infection and diminished quality of life associated with percutaneous leads, incompatible data collection regarding different parameters associated with cardiac function, inability to monitor single vessel throughput and the necessity for continual physician contact to monitor sensor output.

Thus, there exists a need for a wholly implantable blood flow monitoring system to provide early warning to follow blood flow within coronary arteries or bypass grafts and evaluate heart wall motion. Such a blood flow monitor system would allow for the evaluation of new myocardial revascularization processes, allow physician intervention before stenosis or occlusion of a vessel causes CAD complications such as death and allow physicians to follow heart function to see if it improves with treatment.

SUMMARY OF THE INVENTION

A blood flow monitoring system includes an implantable blood flow sensor fixed proximal to the blood vessel to be monitored and an implantable myocardial contractility sensor affixed proximal to a patient's heart wall. A microcontroller is in communication with the blood flow sensor and the contractility sensor to collect data therefrom and couple the data with time stamp information. A radio frequency and/or IR (infrared) transceiver communicates the data and the time stamp information to an external monitor. The external monitor including an electrocardiogram sensor and a second radio frequency and/or IR transceiver for receiving blood flow and contractility data coupled with time stamp information and a microcontroller coupled to the second radio frequency transceiver and the electrocardiogram sensor such that the external monitor microcontroller synchronizes output from the electrocardiogram sensor and implanted sensor data to calculate in combination at least two synchronized parameters from the group of blood flow, heart wall motion and electrocardiogram.

A method of monitoring blood flow and heart function according to the present invention includes measuring blood flow in a blood vessel, measuring myocardial wall motion, measuring an electrocardiogram, synchronizing at least two of the measurements selected from the group consisting of blood flow, myocardial wall motion and electrocardiogram and communicating at least two synchronized measurements to a remote receiver or to a local display in the external monitor. The present invention represents an improved method of monitoring blood flow in coronary arteries or other vessels with an implanted blood flow transit time sensor and heart wall motion with contractility piezoelectric crystal sensors wherein the sensor signals are communicated external to the body by an implanted radio frequency and/or IR transceiver without need of percutaneous leads.

A blood flow monitoring system includes a first electronic interface exciting a blood flow sensor with a first ultrasonic signal and receiving a first reflected ultrasonic signal from the blood flow sensor, a set of second electronic interface exciting a piezoelectric crystal sensor of an implanted array of piezoelectric sensors with a second ultrasonic signal and receiving a second reflected ultrasonic signal from nonexcited piezoelectric sensors of said array. A microcontroller is coupled to each of the first and the second electronic interfaces for computing blood flow and myocardial wall motion, respectively. A radio frequency communication transceiver in communication with an external monitor receives an external reference time stamp information therefrom and transmits stamped blood flow and myocardial wall motion data thereto. The present invention has utility in remote monitoring of patient condition capable of communicating synchronized or unsynchronized cardiac function data and coronary blood flow between an external monitor and a distant, remote location. Patient condition is thereby monitored to prevent complications associated with degenerative blood flow within monitored blood vessels.

BRIEF DESCRIPTION OF THE DRAWINGS

The present invention will be better understood with reference to the following drawings which are intended to be exemplary and in no way limit the scope of the appended claims hereto.

DETAILED DESCRIPTION OF THE PREFERRED EMBODIMENTS

A blood flow monitoring system according to the present invention following surgical implantation affords noninvasive monitoring of blood flow within a single blood vessel or plurality thereof in heart function. In a preferred system, output data is transmitted to a remote location from the patient to his physician for review. In a still more preferred embodiment a physician reviewing cardiac function information remotely is able to communicate by way of the present invention to illustratively: adjust a medicament pump operation to affect a modification of coronary vessel response, modify ventricular assist device operation or modify pacemaker operation. Alternatively, the physician can communicate a warning to the patient by a conventional telecommunications device. The blood flow monitoring system of the present invention has utility in allowing physicians and healthcare providers an early intervention upon a decrease in blood flow within a coronary vessel and/or decrease in myocardial wall motion in order to prevent complications of CAD. The system is also operative in examining and determining normal blood flow parameters in a native coronary artery and the effects thereon of various activities and drugs. Thus, the present invention also has utility in tailoring effective medication and/or exercise regimes for a particular individual. Similarly, the present invention provides information about blood flow in bypass grafts as a function of time from surgery through early postoperative periods and thereafter, allowing for the development of new surgical procedures and computer modeling of optimal bypass graft parameters. Illustrative of these procedures for myocardial revascularization include off-pump beating heart CABG, use of angiogenesis factors, gene therapy of vascular endothelium, transmyocardial revascularization (TMR), miniature prosthetic vascular grafts, anticoagulants and the like. The present invention, unlike an angiogram, can operate continuously, intermittently and/or during episodic periods, is noninvasive subsequent to implantation, uses no harmful imaging dyes, and is cost efficient in centralizing continuous monitoring of numerous patients and can reduce deaths and reduce healthcare costs. The present invention has still further utility once implanted in ruling out cardiac causes of chest pain in CAD patients suffering chest pain.

As used herein the term "proximal" is defined in the context of sensor placement on or about a coronary vessel or myocardial wall to mean in contact with or located within a distance such that the sensor is responsive to the condition of the coronary vessel or myocardial wall.

Figure 1:
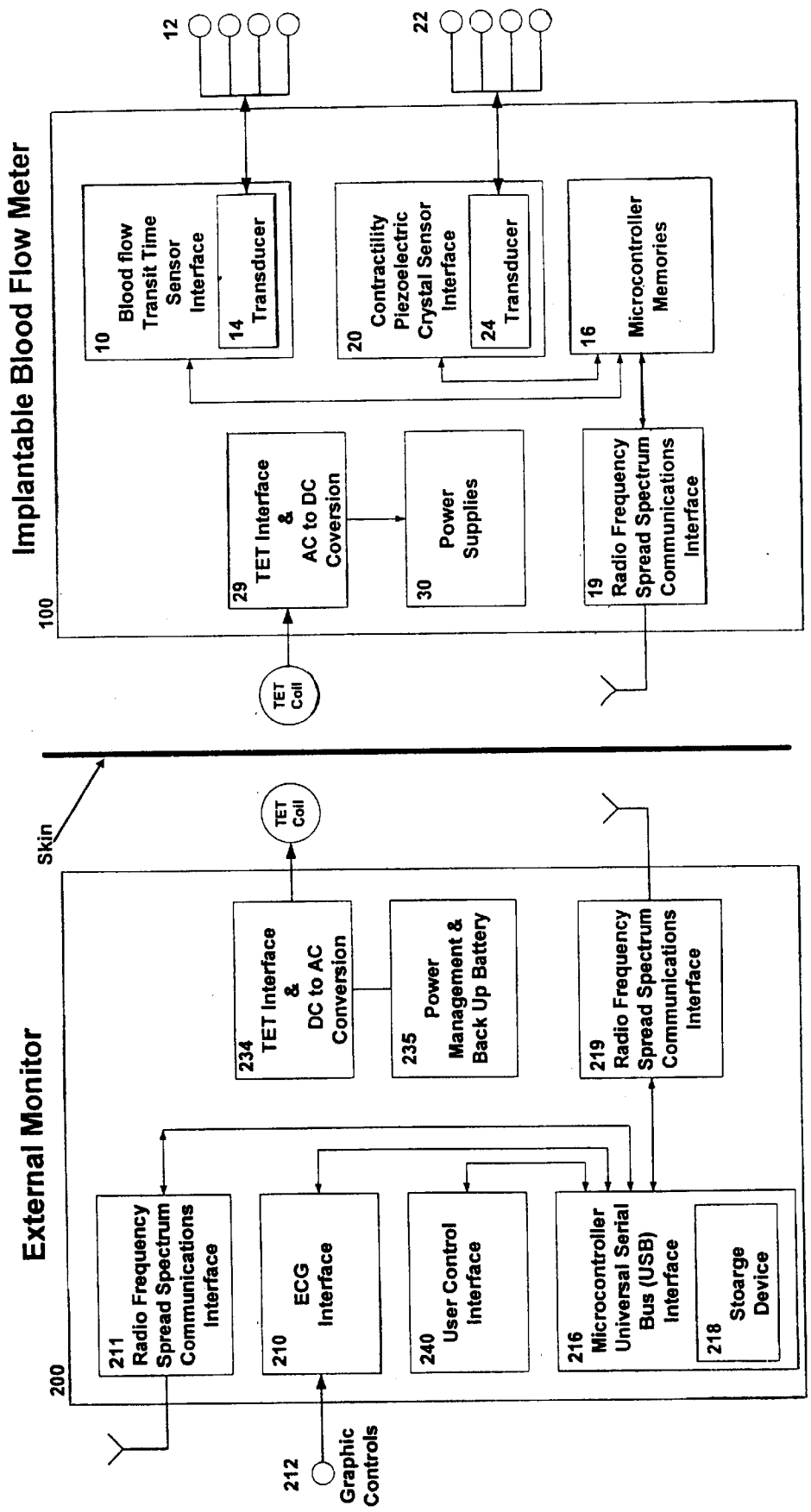
FIG. 1 is a block diagram of a system in accordance with a preferred embodiment of the present invention.

Referring now to FIG. 1 of the drawings, a blood flow monitoring system of the present invention includes an implanted hardware interface 10 in connection with at least one conventional implanted blood flow sensor 12 and other sensors can be incorporated. Preferably, the blood flow sensor 12 is a conventional blood flow transmit time sensor. An exemplary transit time blood flow sensor operative in the present invention includes 25, 2.55, 35, 65, 85, 105 or equivalent and variations of these sensors produced by Transonic System Corp., Ithaca, N.Y., and other sensors can be incorporated if determined to be necessary. More preferably, a plurality of blood flow sensors 12 are implanted in connection with an interface 10. It is appreciated that while blood flow measurement according to the present invention is detailed in regard to a transit time based blood flow sensor, other methods of determining blood flow are operative herein, illustratively including those detailed in U.S. Pat. Nos. 5,865,749; 5,807,258; 5,785,657; 5,598,847; 5,598,841; 5,289,821 and 4,227,407. A blood flow sensor 12 of the present invention is surgically implanted proximal to a native coronary artery or a bypass graft and held in place with conventional tissue adhesive or surgical techniques. Typically, two to five blood flow sensors provide a thorough survey of coronary blood flow within a patient. The interface 10 contains therein an ultrasonic pulse transducer 14 for pulse stimulation of a blood flow sensor 12 and receiving a reflected ultrasonic signal from the sensor 12. Alternatively, the blood flow sensor 12 is replaced with an acoustic, optical or thermal excitation source and detector consistent with the mode of blood flow sensing. Reflected ultrasonic signals are communicated to a microcontroller 16 which contains internal software or external software in the external monitor microcontroller 216 or in the remote receiver for computing blood flow information. A storage device capacity is optionally incorporated into the microcontroller 216 and is capable of storing from at least a few hours to a few days of blood flow monitoring data in event of a system failure or to transfer the monitor information offline to a distant remote RF receiver 66. The output blood flow information from microcontroller 16 is thereafter correlated with time stamp information from a real-time clock within the microcontroller 16 (not shown), which is synchronized with the reference time information from the external monitor, communicated from an external monitor 200 by way of a wireless radio frequency communications transceiver 19 within the implanted blood flow meter portion 100 of the present invention. Thereafter, time stamped blood flow information is communicated to the external monitor 200 by way of the implanted radio frequency transceiver 19. A representative radio frequency transceiver operative in the present invention includes off the shelf spread spectrum radio component or components operating in the unlicensed Industrial, Scientific and Medical (ISM) frequency band, 2.4–2.5 GHz.

A myocardial contractility sensor 22 is also optionally implanted within blood flow meter 100. While myocardial wall motion data is obtainable from sensors operating on a variety of principles including ultrasonic Doppler, piezoelectric crystal sensors, ranging from 0.75 m to 2.3 mm, available from Sonometrics Corporation, London, Ontario, Canada are readily incorporated, preferably, myocardial wall motion is detected using an array of at least two piezoelectric crystal sensors proximal to the myocardium wall of a patient. An operative contractility device according to the present invention is commercially available from Sonometrics Corp., London, Ontario, Canada. The contractility sensor 22 is connected to a contractility interface 20. In the case of a piezoelectric contractility sensor array 22, the contractility interface 20 includes an ultrasonic pulse transducer 24 designed to excite one of the piezoelectric crystal sensors at a time proximal to the myocardium wall with an ultrasonic signal. The transducer 24 thereafter receives ultrasonic signals conveyed from the remaining unexcited piezoelectric crystal sensors. The contractility interface 20 thereafter conveys unexcited sensors signals outputs to a microcontroller (not shown) which is similar to microcontroller 16 with the exception of containing software for the computation of heart wall motion from output ultrasonic signals. The microcontroller 16 by analogy to the blood flow information, microcontroller 16, time stamp the myocardial wall motion information with real-time clock within the microcontroller 16 (not shown). Time stamped heart wall motion information is then exported to the external monitor 200 by way of the radio frequency transceiver 19. It is appreciated that a single microcontroller is operative in the present invention to process blood flow sensor and piezoelectric crystal sensor output to compute blood flow and heart wall motion information, respectively.

A power supply 30 is implanted within the blood flow meter 100 to energize the various components thereof. The power supply 30 is implanted within the blood flow meter 100 to energize the various components thereof. The power supply 30 receives power from the external monitor 200 via the TET interface 29.

The implantable blood flow meter 100 and components thereof are totally implantable without transcutaneous leads or connections which tend to be locations of infection. The implantable blood flow meter 100 optionally has telemetry capabilities via the RF spread spectrum communications interface 19, 219 and 211 to allow for remote monitoring. Blood flow sensors 12 are tunneled above the patient diaphragm and under the lowermost anterior rib and connected to the meter 100 which optionally is placed in a pocket in the left upper quadrant of the lateral abdominal wall. Piezoelectric crystal sensors for the measurement of ventricular function are similarly tunneled and connected to the meter 100. Insertion of the implantable meter 100 as well as blood flow sensors 12 and contractility sensors 22 is performed under general anesthesia and typically occurs upon completion of a conventional coronary artery bypass graft or heart transplant procedure and after the reversal of heparin anticoagulation with protamine. In patients with stable angina or after PTCA, a blood flow sensor and piezoelectric crystals are placed on a patient's heart through a minimally invasive technique using thoracoscopic ports or through a small anterior thoracotomy incision.

The external monitor 200 optionally includes an ECG sensor affixed to a patient's chest in order to supply information about the heart wall rhythm is helpful when evaluating blood flow and heart wall motion. An external ECG probe sensor operative in the present invention includes conventional ECG probes illustratively including F21 silver probe or equivalent from Graphic Control, Buffalo, N.Y. Preferably, ECG information utilized in the present invention is synchronized with blood flow and heart wall motion information communicated by the implantable blood flow meter 100. The ECG sensor 212 is coupled to an ECG interface 210 is customized to transmit ECG information to a microcontroller 216 having interface software and a timer circuit (not shown) for correlating ECG information as obtained from the ECG interface 210 with a time stamp thereby allowing synchronization of ECG, blood flow and contractility information. It is appreciated that ECG data provided by an external monitor synchronized with either myocardial wall motion data or blood flow data alone is satisfactory for many continual cardiac function monitoring purposes.

Transit time measured between the transmitted and the reflected ultrasonic signals are communicated to a microcontroller 16 which contains internal and/or external software for computing blood flow information. A storage device capacity is optionally incorporated into the microcontroller 216 and is capable of storing from at least a few hours to a few days of blood flow monitoring data in event of a critical change in the patient's condition or a system failure or to allow offline communication to a distant RF receiver 66. Preferably, the microcontroller 216 incorporates a conventional universal serial bus or equivalent (not shown) to facilitate communication to other components of the external monitor 200.

The external microcontroller 216 provides reference time stamp information by way of external radio frequency spread spectrum transceiver 219 communicating with implanted transceiver 19 to the implantable blood flow meter microcontroller 16. The external microcontroller 216 provides the reference time stamp information to the microcontroller 16 for time stamping the monitored information.

The external monitor 200 is sized so as to be worn in a waist-borne or shoulder-hung pouch.

Power management circuitry 235 is connected to a power supply (not shown) to operate the various components of the external monitor 200. It is appreciated that a power supply for the external monitor 200 includes battery and it provides power to the implanted blood flow meter 100 via the TET (transcutaneous energy transfer) interface 234. Optionally, power management circuitry 235 further includes self-diagnostic meters capable of indicating excessive current draw and/or resistance of a particular component indicative of malfunction.

The microcontroller 216 communicates, by way of radio frequency transceiver 219 the reference time stamp information to microcontroller 19 to allow it to time stamp the monitored blood flow and contractility information by way of implanted radio transceiver 19. Time stamped blood flow and contractility data is received by the external microcontroller 216 by way of radio transceivers 19 and 219.

External monitor 200 includes a user control interface having functions illustratively including audio output, visual output, digital serial output, and user input controls. The user control interface 240 allows a user to capture continuously or on demand blood flow, heart contractility and/or ECG information. Optionally, the user control interface 240 also controls an implanted pacemaker and the function thereof adjusted in accordance with physician instruction based upon output of the present invention.

Figure 2:
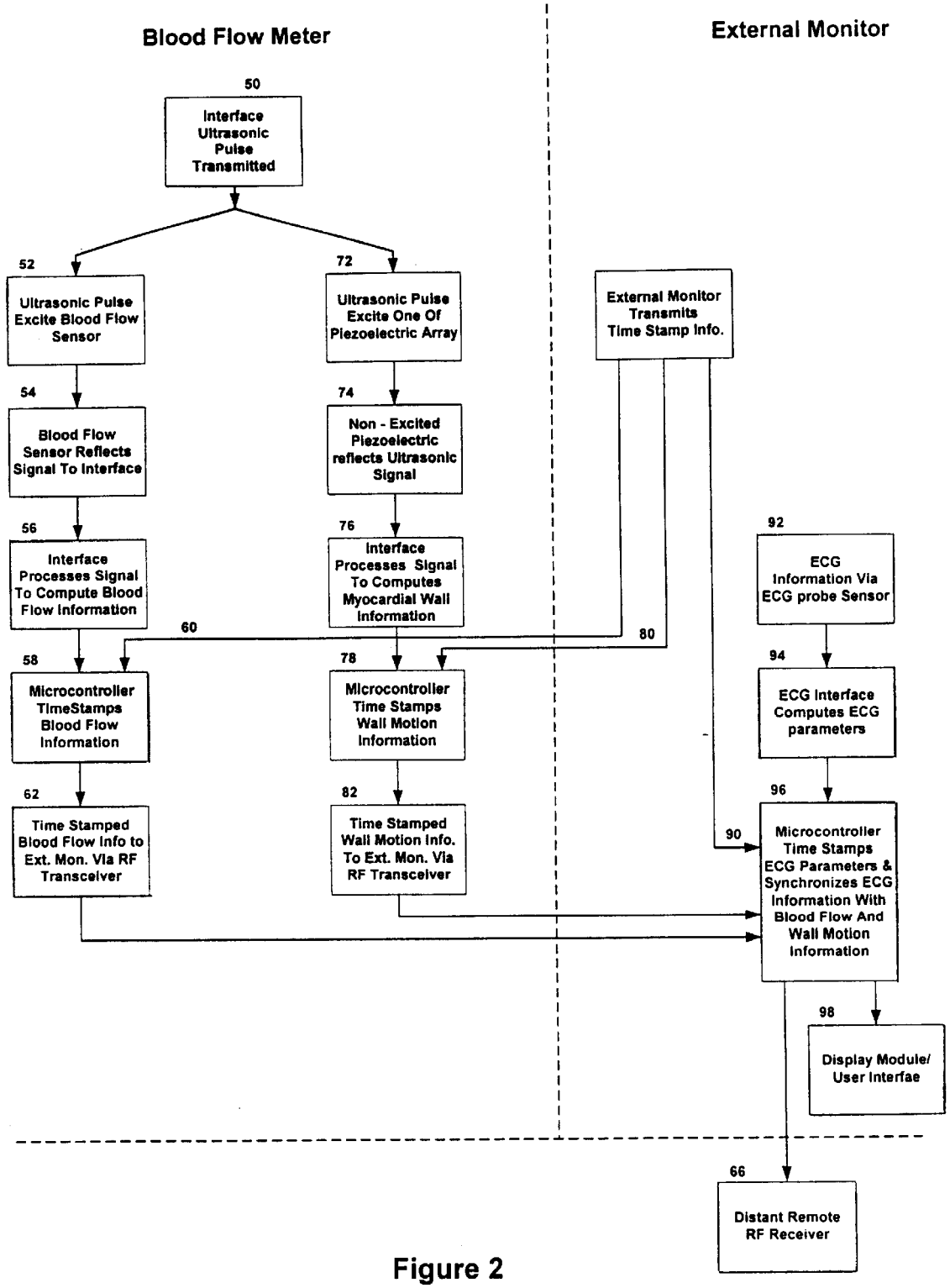
FIG. 2 is a block diagram of related process steps associated with a preferred operative sequence for the present invention.

With reference to FIG. 2, in a preferred embodiment of the present invention, an ultrasonic pulse 50 is transmitted from a blood flow sensor interface to a blood flow sensor located proximal to a coronary artery or bypass graft where the ultrasonic pulse 50 excites the blood flow sensor 52. A reflected signal 54 is from the blood flow sensor back to the blood flow interface. The blood flow sensor reflected signal 54 conveys transit time information about blood flow within a vessel proximal to the blood flow sensor. The blood flow sensor reflected signal 54 to the interface is processed within an implanted interface 56 to compute blood flow information 56. The computed blood flow information 56 is time stamped by the microcontroller 58. The reference time stamp information being fed to the blood flow microcontroller 19 from the external monitor microcontroller 216. Reference time information is transmitted 60 to the blood flow microcontroller by way of radio frequency transceivers located external and implanted within the patient's body. Time stamped blood flow information which is correlated with time stamp data is then transmitted to an external monitor by the radio frequency transceiver communication link between the implanted device and an external monitor 62. Time stamped blood flow information 62 is synchronized by the microcontroller 96 and then displayed from the external monitor by way of the user control interface and display module 98. Optionally, synchronized blood flow information 98 is transmitted from the external monitor to a distant remote radio frequency receiver 66.

An interface ultrasonic pulse 50 is also transmitted to one of an array of piezoelectric crystal sensors 72 located proximal to the myocardial wall. The vibration associated with exciting a piezoelectric sensor is sensed by unexcited piezoelectric crystal sensors causing reflected ultrasonic signal 74 to be returned to the interface. It is appreciated that the blood flow interface and piezoelectric crystal sensor interface are alternatively incorporated into a single interface or operative as two independently functioning interface components with independent ultrasonic transducers. Thereafter, the piezoelectric crystal sensor reflected signal 74 is processed within an implanted microcontroller to compute myocardial wall motion information 76. It is appreciated that the implanted microcontroller computing blood flow information and the microcontroller computing myocardial wall motion information are alternatively a unified single microcontroller or two independently functioning microcontroller components. Myocardial wall motion information is thereafter time stamped by microcontroller 78 of the blood flow meter 100. The reference time stamp information being conveyed from a microcontroller of an external monitor by way of an external radio frequency transceiver and an implanted radio frequency transceiver communications interface 80. Time stamped wall motion information 82 is thereafter transmitted to the external monitor by way of the same radio frequency and/or other method of wireless communications interface. Synchronized wall motion information 82 is available for display from the external monitor by way of a user control interface 84. Optionally, synchronized wall motion data 96 is transmitted to a distant remote radio frequency receiver 66.

External to the body of a recipient of the present invention, an ECG probe sensor is adhered to the chest. ECG information from the probe sensor 92 is transmitted to an ECG interface 94 to obtain ECG parameters 94. ECG parameters are time stamped with time stamp data 96. The time stamp data is obtained from the microcontroller located within the external monitor 90. Synchronized ECG information 96 is displayed from the external monitor 98 and optionally transmitted to a distant remote radio frequency receiver 66. While the embodiments of the present invention depicted in FIGS. 1 and 2 include the time stamped of blood flow 62, myocardial wall motion 82, and ECG information 96, it is appreciated that the synchronization of, and/or the monitoring of, any two of the three aforementioned cardiac parameters is often sufficient to adequately monitor heart function of a given individual.

A distant remote radio frequency receiver to which synchronized cardiac information is transmitted serves to allow physician monitoring of cardiac function. Further, a distant remote radio frequency receiver in communication with the user interface of an external monitor communicates information thereto in regard to medication dosages, lifestyle modification, pacemaker settings and the like or alternatively, the patient receives a conventional communication indicating the need for a lifestyle modification. It is further appreciated that a centralized distant remote radio frequency receiver is well suited for receiving cardiac function status from numerous systems of the present invention thereby making continuous monitoring of an inventive system at a remote location a cost effective endeavor.

Any publications or patents mentioned in this specification are indicative of the skill level in the art to which the invention pertains. These publications and patents are herein incorporated by reference to the same extent as if each individual publication or patent was specifically and individually indicated to be incorporated by reference.

Various modifications of the instant invention in addition to those shown and described herein will be apparent to those skilled in the art of the above description. Such modifications are also intended to fall within the scope of the appended claims.

What is claimed is:

1. A blood flow monitoring system comprising:
   an implantable blood flow sensor;
   an implantable myocardial contractility sensor;
   a first microcontroller in communication with said blood flow sensor and said conductility sensor collecting data from said blood flow sensor and said contactility sensor, wherein the data is coupled with time stamp information; and
   a first radio frequency transceiver communicating the data and the time stamp information to an external monitor, said external monitor comprising:
      an elecmocardiogram sensor;
      a second radio frequency transceiver receiving the data and time stamp information;
      a third radio fluency transceiver transmitting the time stamped or synchronized information to a distant receiver; and
      a microcontroller coupled to said second and third transceivers and said electrocardiogram sensor, wherein said microcontroller synchronizes output from said electrocardiogram sensor and the data to calculate in combination at least two synchronized parameters selected from a group consisting of blood flow, heart wall motion and electrocardiogram.

2. The blood flow monitoring system of claim 1 wherein said myocardial contractility sensor is a piezoelectric crystal.

3. The blood flow monitoring system of claim 1 further comprising an implantable microcontroller manipulating the data and the time stamp information prior to communicating by said first radio frequency transceiver.

4. The blood flow monitoring system of claim 1 wherein said first radio frequency transceiver is implanted.

5. The blood flow monitoring system of claim 1 further comprising a radio frequency communication system between said external monitor and an implanted blood flow meter.

6. The blood flow monitoring system of claim 1 further comprising a radio frequency communication system between said external monitor and a distant remote receiver.

7. A method of monitoring blood flow comprising the steps of:

measuring a blood flow in blood vessels;

measuring a myocardial wall motion;

measuring an electrocardiogram using an external monitor;

synchronizing at least two measurements selected from a group consisting of, blood flow, myocardial wall motion and electrocardiogram; and communicating at least two synchronized measurements to an external monitor and to a distant remote receiver.

8. The method of claim 7 wherein the blood flow is measured with a first ultrasonic signal reflected from the blood vessel to a blood flow sensor.

9. The method of claim 8 wherein said blood flow sensor is implanted.

10. The method of claim 8 wherein the first ultrasonic signal reflected is processed by an implanted microcontroller.

11. The method of claim 10 further comprising time stamping the first ultrasonic signal reflected.

12. The method of claim 7 wherein the myocardial wall motion is measured with an implanted ultrasonically excited piezoelectric crystal sensor with a second ultrasonicaly reflected signal being received by at least one implanted ultrasonically unexcited piezoelectric sensor.

13. The method of claim 12 wherein the second reflected ultrasonic signal is processed by an implanted microcontroller.

14. The method of claim 13 further comprising time stamping the second reflected ultrasonic signal.

15. The method of claim 13 wherein an integrated microcontroller processes the second reflected ultrasonic signal and a first signal reflected from the blood vessel to a blood flow sensor relating to blood flow.

16. The method of claim 7 wherein the at least two synchronized measurements are communicated with a radio frequency transceiver.

17. The method of claim 16 wherein said radio frequency transceiver is implanted.

18. The method of claim 16 wherein said radio frequency transceiver communicates time stamped blood flow data.

19. The method of claim 16 wherein said radio frequency transceiver communicates time stamped myocardial wall motion data.

20. The method of claim 7 further comprising the step of: transmitting output of said external display monitor to a distant radio frequency receiver.

21. A blood flow monitoring system comprising:

a first electronic interface exciting a blood flow sensor with a first ultrasonic signal and receiving a first reflected ultrasonic signal from said blood flow sensor;

a second electronic interface exciting a piezoelectric crystal sensor of an implanted array of piezoelectric sensors with a second ultrasonic signal and receiving a second reflected ultrasonic signal from non-excited piezoelectric sensors of said array;

a microcontroller coupled to said first electronic interface for computing blood flow and to said second electronic interface for computing myocardial wall motion; and a radio frequency communication transceiver in communication with an external monitor receiving external time stamp synchronization data therefrom and transmitting synchronized blood flow and myocardial wall motion data thereto.

22. The system of claim 21 further comprising a plurality of blood flow sensors.

23. The system of claim 21 wherein said first and said second electronic interfaces form a unitary interface.

24. The system of claim 21 further comprising an external electrocardiogram system synchronized with blood flow and myocardial wall motion data.

25. The system of claim 24 further comprising a distant remote receiver able to receive the synchronized electrocardiogram, blood flow and myocardial wall motion data.

* * * * *

UNITED STATES PATENT AND TRADEMARK OFFICE
CERTIFICATE OF CORRECTION

PATENT NO.    : 6,458,086 B1
DATED         : October 1, 2002
INVENTOR(S)   : Kenneth Lawrence Franco It is certified that error appears in the above-identified patent and that said Letters Patent is hereby corrected as shown below:

Column 1,
Line 38, after "annually" delete -- with --.
Line 39, after "therefrom" insert -- . --.
Line 39, replace "worldwide" with -- Worldwide --.
Line 39, after "Worldwide" delete "with"

Column 5,
Line 48, replace "interface" with -- interfaces --.

Column 6,
Line 45, replace "includes battery" with -- includes a battery --.
Line 52, replace "communicated," with -- communicates --.

Column 7,
Line 14, replace "being fed" with -- is being fed --.

Column 8,
Line 39, replace "conductility" with -- contractility --.
Line 46, replace "elecmocardio gram" with -- electrocardigram --.
Line 44, replace "monitor," with -- monitor; --.
Line 49, replace "fluency" with -- frequency --.

Column 9,
Line 16, replace "of" with -- of: --.
Line 32, replace "ultrasonicaly" with -- ultrasonically --.

Signed and Sealed this

Eighteenth Day of March, 2003

JAMES E. ROGAN
*Director of the United States Patent and Trademark Office*